(12) United States Patent
Komazaki et al.

(10) Patent No.: US 8,186,864 B2
(45) Date of Patent: May 29, 2012

(54) LIGHT SOURCE DEVICE

(75) Inventors: Iwao Komazaki, Saitama (JP); Eiji Yamamoto, Ome (JP)

(73) Assignee: Olympus Corporation, Tokyo (JP)

( * ) Notice: Subject to any disclaimer, the term of this patent is extended or adjusted under 35 U.S.C. 154(b) by 258 days.

(21) Appl. No.: 12/651,648

(22) Filed: Jan. 4, 2010

(65) Prior Publication Data

US 2010/0172148 A1 Jul. 8, 2010

(30) Foreign Application Priority Data

Jan. 7, 2009 (JP) ................................. 2009-001992

(51) Int. Cl.
*A61B 1/06* (2006.01)
*F21S 4/00* (2006.01)
*F21V 5/00* (2006.01)
*G02B 6/06* (2006.01)
*A41F 1/00* (2006.01)
*H01L 33/00* (2010.01)
*H01J 5/16* (2006.01)

(52) U.S. Cl. ........ 362/572; 362/555; 362/558; 362/581; 362/583

(58) Field of Classification Search .................. 362/572, 362/558, 555, 581, 583
See application file for complete search history.

(56) References Cited

U.S. PATENT DOCUMENTS

| 4,329,737 | A | * | 5/1982 | Triller et al. ................... 362/555 |
| 6,151,769 | A | * | 11/2000 | Bliss et al. ........................ 29/600 |
| 2002/0186921 | A1 | * | 12/2002 | Schumacher et al. .......... 385/31 |
| 2003/0021098 | A1 | * | 1/2003 | Chang .............................. 362/19 |
| 2007/0092184 | A1 | * | 4/2007 | Hama et al. ...................... 385/76 |
| 2007/0195538 | A1 | * | 8/2007 | Hama et al. ..................... 362/382 |
| 2008/0075406 | A1 | * | 3/2008 | Kadomi et al. .................. 385/79 |
| 2008/0089089 | A1 | * | 4/2008 | Hama et al. ..................... 362/574 |
| 2008/0117620 | A1 | * | 5/2008 | Hama et al. ...................... 362/84 |

FOREIGN PATENT DOCUMENTS

JP 2003-19112 1/2003

* cited by examiner

*Primary Examiner* — Jong-Suk (James) Lee
*Assistant Examiner* — David J Makiya
(74) *Attorney, Agent, or Firm* — Scully, Scott, Murphy & Presser, P.C.

(57) ABSTRACT

A light source device includes an excitation light source which generates excitation light, a fluorescent member containing a fluorescent substance which absorbs the excitation light to generate fluorescence, an emitting side optical member which is provided on an emitting end face of the fluorescent member, and a reflector which is provided on the side surface of the fluorescent member. The reflector has an optical property of reflecting the excitation light and the fluorescence. The emitting side optical member has an optical property of reflecting the excitation light and transmitting the fluorescence.

2 Claims, 6 Drawing Sheets

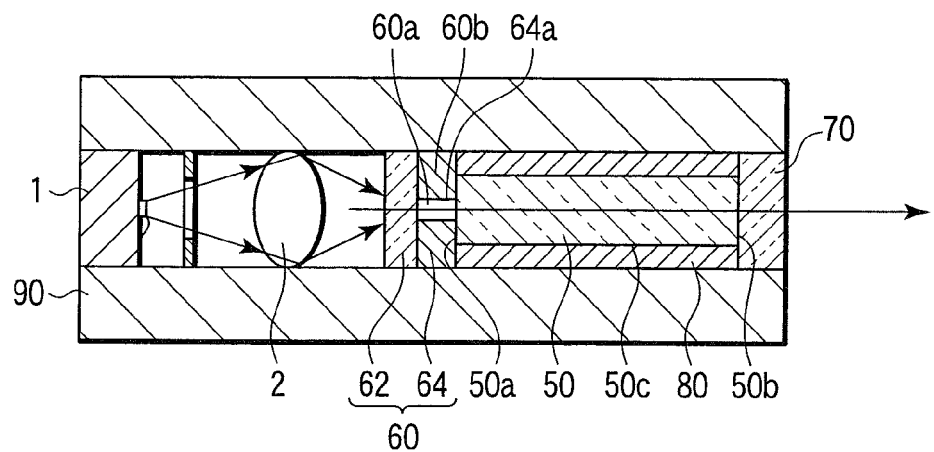
F I G. 1
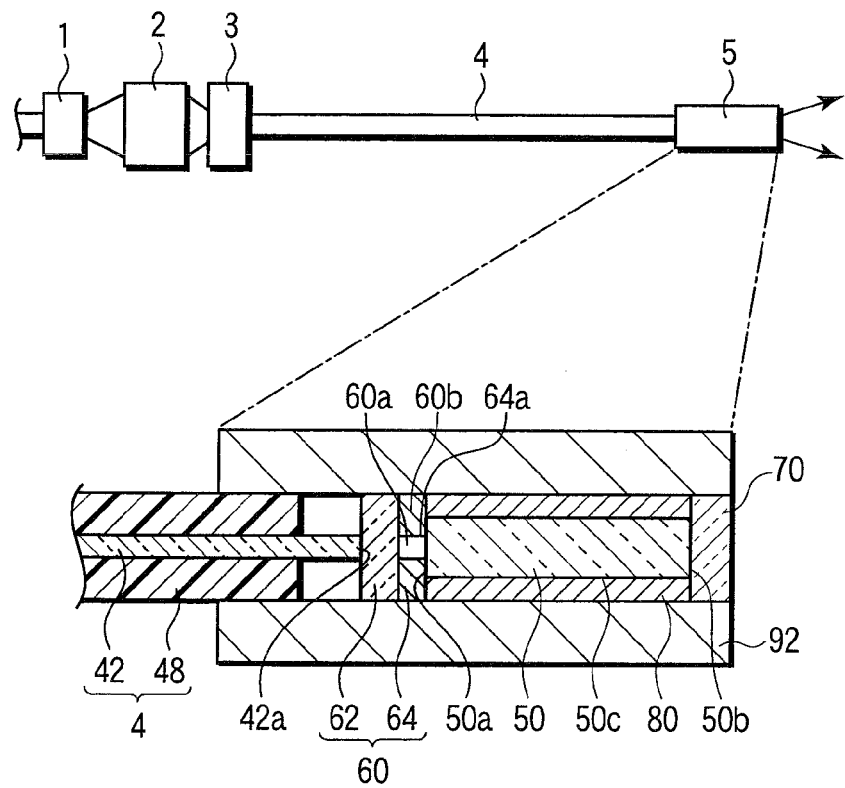
F I G. 2

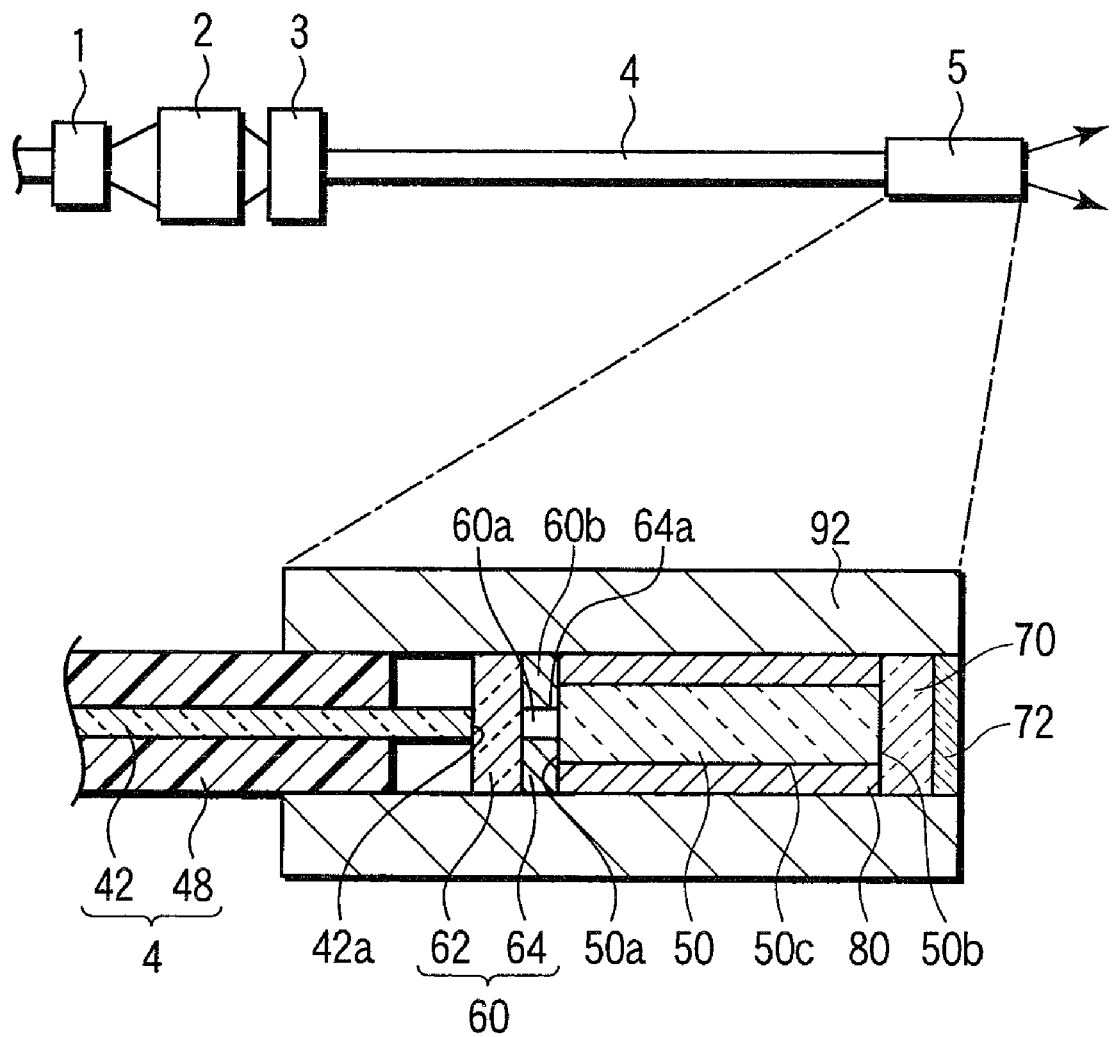
F I G. 7

LIGHT SOURCE DEVICE

CROSS-REFERENCE TO RELATED APPLICATIONS

This application is based upon and claims the benefit of priority from prior Japanese Patent Application No. 2009-001992, filed Jan. 7, 2009, the entire contents of which are incorporated herein by reference.

BACKGROUND OF THE INVENTION

1. Field of the Invention

The present invention relates to a light source device.

2. Description of the Related Art

A light source device which uses fluorescence is known as a light source device to be suitably combined with an industrial or medical endoscope. For example, Jpn. Pat. Appln. KOKAI Publication No. 2003-19112 discloses an endoscopic apparatus equipped with such a light source device. This endoscopic apparatus is shown in FIG. 10.

An endoscopic insertion portion 100 includes an illumination optical system at the front end. The illumination optical system 103 is connected to an illumination unit 110 through a light guide 101. The illumination unit 110 includes three LED light sources 111, 112, and 113 for emitting ultraviolet light, fluorescent fibers 114, 115, and 116 for respectively generating red light (R light), green light (G light), and blue light (B light) for the radiation of the ultraviolet light emitted from the LED light sources 111, 112, and 113, and dichroic mirrors 117, 118, 119, and 120 for controlling the reflection and transmission of the R light, the G light, and the B light generated from the fluorescent fibers 114, 115, and 116.

The dichroic mirror 117 has a property of reflecting light in the wavelength region of the R light generated from the fluorescent fiber 114. The dichroic mirror 118 has a property of transmitting the light in the wavelength region of the R light generated from the fluorescent fiber 114 and reflecting light in the wavelength region of the G light generated from the fluorescent fiber 115. The dichroic mirror 119 has a property of transmitting light in the wavelength regions of the G light generated from the fluorescent fiber 115 and the R light which has traveled through the fluorescent fiber 115, and reflecting light in the wavelength region of the B light generated from the fluorescent fiber 116. The dichroic mirror 120 has a property of transmitting light in the wavelength regions of the B light generated from the fluorescent fiber 116 and the R light and the G light which have traveled through the fluorescent fiber 116, and reflecting light in the wavelength region of the ultraviolet light (excitation light).

The light in the wavelength regions of the R light, the G light, and the B light which has passed through the dichroic mirror 120 is guided to the illumination optical system 103 by the light guide 101, and radiated from the illumination optical system 103.

In this embodiment, part of the fluorescence generated from the fluorescent fibers 114, 115, and 116, is only used for illumination. That is, the fluorescent or excitation light traveling in the side surface directions of the fluorescent fibers 114, 115, and 116 is radiated from the side surfaces not to be used. Therefore, the efficiency of the use of the excitation light for the generation of fluorescence is low, and the efficiency of the use of the fluorescence for illumination is low.

BRIEF SUMMARY OF THE INVENTION

The present invention has been made in consideration of these situations, and an object of the present invention is to provide a light source device which has a high efficiency of the use of the excitation light for the generation of fluorescence and a high efficiency of the use of the fluorescence for illumination.

A light source device includes an excitation light source which generates excitation light, a fluorescent member containing a fluorescent substance which absorbs the excitation light to generate fluorescence, an emitting side optical member which is provided on an emitting end face of the fluorescent member, and a reflector which is provided on the side surface of the fluorescent member. The reflector has an optical property of reflecting the excitation light and the fluorescence. The emitting side optical member has an optical property of reflecting the excitation light and transmitting the fluorescence.

According to the present invention, a light source device which has a high efficiency of the use of the excitation light for the generation of fluorescence and a high efficiency of the use of the fluorescence for illumination is provided.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 shows a light source device according to a first embodiment of the present invention;

FIG. 2 shows a light source device according to a second embodiment of the present invention;

FIG. 7 shows a light source device according to a seventh embodiment of the present invention;

DETAILED DESCRIPTION OF THE INVENTION

Figure 3:
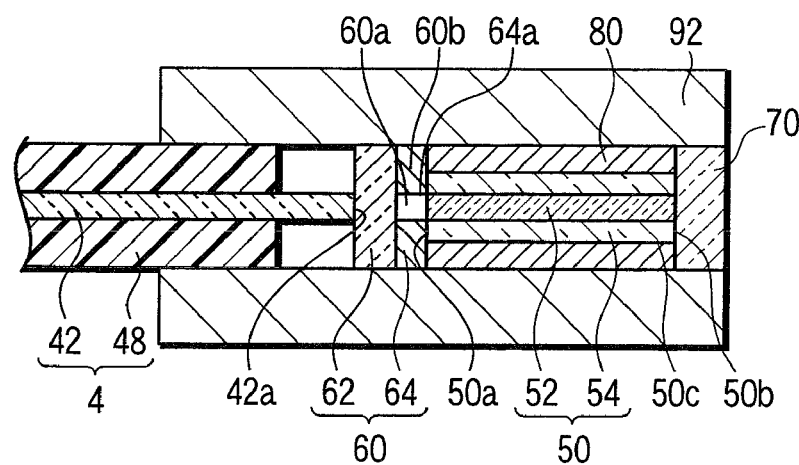
FIG. 3 shows a wavelength converting section of a light source device according to a third embodiment of the present invention.

Embodiments of the present invention will hereinafter be described with reference to the drawings.

First Embodiment

A light source device according to a first embodiment of the present invention is shown FIG. 1.

<Organization>

The light source device in this embodiment includes an excitation light source 1 for generating excitation light, and an optical beam focusing system 2 for focusing the excitation light generated from the excitation light source 1. The excitation light source 1 is composed of, for example, a semiconductor laser, a super luminescent diode, or a light emitting diode. The optical beam focusing system 2 is composed of, for example, a lens having positive power such as a convex lens. The excitation light source 1 and the optical beam focusing system 2 are contained in a cylindrical fixing protective portion 90, and are arranged coaxially with each other.

The light source device also includes a fluorescent member 50 containing a fluorescent substance which absorbs excitation light to generate fluorescence. The fluorescent member 50 is made of a material in which the fluorescent substance is doped in a resin such as a silicon resin or an epoxy resin transparent to the excitation light. The fluorescent member 50 is columnar, and is disposed coaxially with the cylindrical fixing protective portion 90. In the present specification, of two parallel end faces of the fluorescent member 50, the end face located on the side of the excitation light source 1 is referred to as an incident end face 50*a*, and the opposite end face is referred to as an emitting end face 50*b*. Moreover, part of the surface of the fluorescent member 50 excluding the incident end face 50*a* and the emitting end face 50*b* is referred to as a side surface 50*c*. Further, more generally, the side of the excitation light source 1 is referred to as an incident end side, and the other side is referred to as an emitting end side.

The light source device further includes an incident side optical member 60 provided on the incident end face 50*a* of the fluorescent member 50, an emitting side optical member 70 provided on the emitting end face 50*b* of the fluorescent member 50, and a reflector 80 provided on the side surface 50*c* of the fluorescent member 50. The fluorescent member 50, the incident side optical member 60, the emitting side optical member 70, and the reflector 80 are integrally contained in the cylindrical fixing protective portion 90.

The reflector 80 has an optical property of reflecting excitation light and fluorescence. The reflector 80 is cylindrical, and has a reflecting film inside the cylinder. This reflecting film has a high reflectance for the excitation light and fluorescence. In one example, the reflecting film may be made of a metal film. In another example, the reflecting film may be made of a stack film composed of a metal film and a dielectric film. The cylindrical reflector 80 has an inside diameter slightly greater than the outside diameter of the columnar fluorescent member 50, and the columnar fluorescent member 50 is inserted in the cylindrical reflector 80.

The incident side optical member 60 has a transmission portion 60*a* for transmitting the excitation light, and a reflection portion 60*b* for reflecting the excitation light and fluorescence. The incident side optical member 60 includes a disk-shaped glass plate 62 transparent to the excitation light, and a reflection film 64 which is formed on the surface of the glass plate 62 opposite to the excitation light incident surface, and which has an opening 64*a* in the center. In the incident side optical member 60 having this structure, the reflection film 64 forms the reflection portion 60*b*, and the opening 64*a* of the reflection film 64 forms the transmission portion 60*a*. The reflection film 64 has a high reflectance for the excitation light and fluorescence. In one example, the reflection film 64 may be made of a metal film. In another example, the reflection film 64 may be made of a stack film composed of a metal film and a dielectric film. Such an incident side optical member 60 can be created by, for example, a semiconductor process.

The emitting side optical member 70 has an optical property of reflecting excitation light and transmitting fluorescence. The emitting side optical member 70 is made of, for example, a stack film of dielectric layers.

<Operation>

The excitation light emitting from the excitation light source 1 is focused by the optical beam focusing system 2, and enters the fluorescent member 50 through the transmission portion 60*a* of the incident side optical member 60, that is, the opening 64*a* of the reflection film 64. Part of the excitation light which has entered the fluorescent member 50 is absorbed by the fluorescent substance. The fluorescent substance which has absorbed the excitation light generates fluorescence. The fluorescence generated from the fluorescent substance has a wavelength different from the wavelength of the excitation light, more superficially, a wavelength longer than the wavelength of the excitation light. In other words, the wavelength of the excitation light is converted. The fluorescence travels substantially equally in all directions. A part of the fluorescence travels toward the reflector 80. Another part of the fluorescence travels toward the incident side optical member 60. Still another part of the fluorescence travels toward the emitting side optical member 70. The fluorescence which has entered the reflector 80 is reflected by the reflector 80, and then again travels in the fluorescent member 50. The fluorescence which has entered the reflection portion 60*b* of the incident side optical member 60, is also reflected by the reflection film 64 in the incident side optical member 60, and then again travels in the fluorescent member 50. Moreover, the fluorescence which has entered the emitting side optical member 70 penetrates the emitting side optical member 70 and then emits from the emitting side optical member 70. Thus, the fluorescence is repeatedly reflected by the reflector 80 and the reflection film 64 and travels in the fluorescent member 50 before entering the emitting side optical member 70.

Another part of the excitation light which has entered the fluorescent member 50 is reflected or scattered by the fluorescent substance or the resin. Part of the reflected or scattered excitation light travels toward the emitting side optical member 70. Another part travels toward the reflector 80. Still another part travels toward the incident side optical member 60. The excitation light which has entered the emitting side optical member 70 is reflected by the emitting side optical member 70. The excitation light which has entered the reflector 80 is reflected by the reflector 80. The excitation light which has entered the reflection portion 60*b* of the incident side optical member 60 is reflected by the reflection film 64 in the incident side optical member 60. The excitation light reflected by the emitting side optical member 70, the reflector 80 and the reflection film 64 again travels in the fluorescent member 50, and is absorbed by the fluorescent substance or is reflected or scattered by the fluorescent substance or the resin. Thus, the excitation light is repeatedly reflected by the emitting side optical member 70, the reflector 80, and the reflection film 64 and travels in the fluorescent material 50.

<Advantage>

In the light source device of this embodiment, the excitation light is repeatedly reflected and travels in the fluorescent member 50, so that the efficiency of the use of the excitation light for the generation of fluorescence improves. Moreover, the fluorescence is repeatedly reflected and travels in the fluorescent member 50 before entering the emitting side optical member 70, so that the fluorescence is efficiently guided to the emitting side optical member 70, and the efficiency of the use of the fluorescence for illumination improves.

<Modifications>

While the incident side optical member 60 is provided on the incident end face 50a of the fluorescent member 50 in this embodiment, the incident side optical member 60 can be omitted.

That is, as described above, the excitation light which has entered the fluorescent member 50 is reflected or scattered by the fluorescent substance or the resin in the fluorescent member 50 and then travels in various directions. However, as the excitation light enters the fluorescent member 50 from the incident end face 50a to the emitting end face 50b, the amount of the excitation light which is reflected and thus travels toward the incident end face 50a is much smaller than the amount of the excitation light which is scattered and thus travels toward the side surface 50c or the amount of the excitation light which travels toward the emitting end face 50b. Therefore, the efficiency of the use of the excitation light significantly improves even without the incident side optical member 60.

Second Embodiment

A light source device according to a second embodiment of the present invention is shown FIG. 2. In FIG. 2, components provided with the same reference numbers as the components shown in FIG. 1 are similar components and are not described in detail.

<Organization>

The light source device in this embodiment includes an excitation light source 1 for generating excitation light, an optical beam focusing system 2 for focusing the excitation light generated from the excitation light source 1, an optical fiber code 4 for guiding the excitation light, and a wavelength converting section 5 for converting the wavelength of the excitation light emitted from the emitting face of the optical fiber code 4. A fiber connector 3 is provided at the end of the optical fiber code 4 on the incident end side, and the optical fiber code 4 is optically coupled to the optical beam focusing system 2 by the fiber connector 3. The end of the optical fiber code 4 on the emitting end side is linked to the wavelength converting section 5.

The wavelength converting section 5 includes a fluorescent member 50, an incident side optical member 60, an emitting side optical member 70, a reflector 80, and a fixing protective portion 92. The fluorescent member 50, the incident side optical member 60, the emitting side optical member 70, and the reflector 80 are substantially the same as the equivalents described in the first embodiment. The fluorescent member 50, the incident side optical member 60, the emitting side optical member 70, and the reflector 80 are integrally contained in the cylindrical fixing protective portion 92. The columnar fluorescent member 50 is disposed coaxially with the cylindrical fixing protective portion 92.

The end of the optical fiber code 4 on the emitting end side is inserted and fixed in the cylindrical fixing protective portion 92. The optical fiber code 4 has an optical fiber 42, and an envelope 48 protecting the optical fiber 42. The optical fiber 42 is a single-wire optical fiber composed of a core and a clad. An end face 42a of the optical fiber 42 on the emitting end side is in contact with the incident side optical member 60. The optical fiber 42 is disposed in alignment with a transmission portion 60a of the incident side optical member 60, that is, an opening 64a of the reflection film 64. The optical fiber 42 has a diameter of approximately 100 to 300 μm, and the diameter of the opening 64a is designed to be substantially equal to the diameter of the optical fiber 42.

<Operation>

The excitation light emitting from the excitation light source 1 is focused by the optical beam focusing system 2, enters the fiber connector 3, and is guided to the wavelength converting section 5 by the optical fiber 42. The excitation light guided to the wavelength converting section 5 emits from the emitting side end face 42a of the optical fiber 42, and enters the fluorescent member 50 through the transmission portion 60a of the incident side optical member 60, that is, the opening 64a of the reflection film 64. The behavior of the excitation light after entering the fluorescent member 50 is similar to the behavior in the first embodiment.

That is, part of the excitation light which has entered the fluorescent member 50 is absorbed by the fluorescent substance. The fluorescent substance which has absorbed the excitation light generates fluorescence. The fluorescence generated from the fluorescent substance is repeatedly reflected by the reflector 80 and the reflection film 64 and travels in the fluorescent member 50 before entering the emitting side optical member 70.

Another part of the excitation light which has entered the fluorescent member 50 is reflected or scattered by the fluorescent substance or the resin. The reflected or scattered excitation light is repeatedly reflected by the emitting side optical member 70, the reflector 80, and the reflection film 64 and travels in the fluorescent member 50.

<Advantage>

As in the first embodiment, the excitation light is repeatedly reflected and continues traveling in the fluorescent member 50 in the light source device of this embodiment. Thus, the efficiency of the use of the excitation light for the generation of fluorescence improves. Moreover, the fluorescence is repeatedly reflected and continues traveling in the fluorescent member 50 before entering the emitting side optical member 70, so that the fluorescence is efficiently guided to the emitting side optical member 70, and the efficiency of the use of the fluorescence for illumination improves.

Third Embodiment

A wavelength converting section of a light source device according to a third embodiment of the present invention is shown FIG. 3. In FIG. 3, components provided with the same reference numbers as the components shown in FIG. 2 are similar components and are not described in detail.

The light source device in this embodiment is much the same in organization as the light source device in second embodiment. Parts different from the parts in the second embodiment are chiefly described below.

<Organization>

In the light source device of this embodiment, a fluorescent member 50 includes a high refractive index region 52 extending from an incident end face 50a to an emitting end face 50b, and a low refractive index region 54 surrounding the high refractive index region 52 to extend from the incident end face 50a to the emitting end face 50b. That is, the fluorescent member 50 has a double structure composed of the high refractive index region 52 and the low refractive index region 54. A fluorescent substance is doped in the high refractive index region 52, but no fluorescent substance is doped in the low refractive index region 54. In other words, the fluorescent substance is partially doped in the fluorescent material 50, and the region where the fluorescent substance is doped extends from the incident end face 50a to the emitting end face 50b. The high refractive index region 52 has a diameter of approximately 100 to 300 μm, which is substantially equal to the diameter of an optical fiber 42. The high refractive index region 52 is disposed in alignment with a transmission portion 60a of an incident side optical member 60, that is, an opening 64a of a reflection film 64. Thus, the optical fiber 42 is aligned with the high refractive index region 52 via the transmission portion 60a of the incident side optical member 60.

<Operation>

In the light source device of this embodiment, the excitation light, which has emitted from the emitting side end face 42a of the optical fiber 42, enters the high refractive index region 52 of the fluorescent member 50 through the transmission portion 60a of the incident side optical member 60, that is, the opening 64a of the reflection film 64. The fluorescent member 50 has a double structure in which the low refractive index region 54 is disposed outside the high refractive index region 52. Thus, the excitation light which has entered the high refractive index region 52 is mainly reflected by the interface between the high refractive index region 52 and the low refractive index region 54 and, at the same time, travels in the high refractive index region 52. That is, most of the excitation light is confined in the high refractive index region 52.

Part of the excitation light traveling in the high refractive index region 52 is absorbed by the fluorescent substance, and the fluorescent substance which has absorbed the excitation light generates fluorescence. The fluorescence is repeatedly reflected by the interface between the high refractive index region 52 and the low refractive index region 54, by the reflector 80 and by the reflection film 64, and travels in the fluorescent member 50 before entering the emitting side optical member 70.

Another part of the excitation light traveling in the high refractive index region 52 is reflected or scattered by the fluorescent substance or the resin in the high refractive index region 52, emits from the high refractive index region 52, and enters the low refractive index region 54. Still another part of the excitation light travels in the high refractive index region 52. The excitation light which travels in the high refractive index region 52 is eventually reflected by the emitting side optical member 70. Moreover, the excitation light which has entered the low refractive index region 54 is reflected by the reflector 80, the reflection film 64 and the emitting side optical member 70. Part of the reflected excitation light again enters the high refractive index region 52, and is then confined in the high refractive index region 52. Thus, the excitation light is repeatedly reflected by the interface between the high refractive index region 52 and the low refractive index region 54, by the emitting side optical member 70, by the reflector 80 and by the reflection film 64, and travels in the fluorescent member 50. Moreover, the excitation light has a strong tendency to be confined in the high refractive index region 52.

<Advantage>

In the light source device of this embodiment, the excitation light is repeatedly reflected and travels in the fluorescent member 50. Moreover, the excitation light has a strong tendency to be confined in the high refractive index region 52 in which the fluorescent substance is doped. Thus, the efficiency of the use of the excitation light for the generation of fluorescence improves. Further, the fluorescence is repeatedly reflected and continues traveling in the fluorescent member 50 before entering the emitting side optical member 70, so that the fluorescence is efficiently guided to the emitting side optical member 70, and the efficiency of the use of the fluorescence for illumination improves.

Fourth Embodiment

Figure 4:
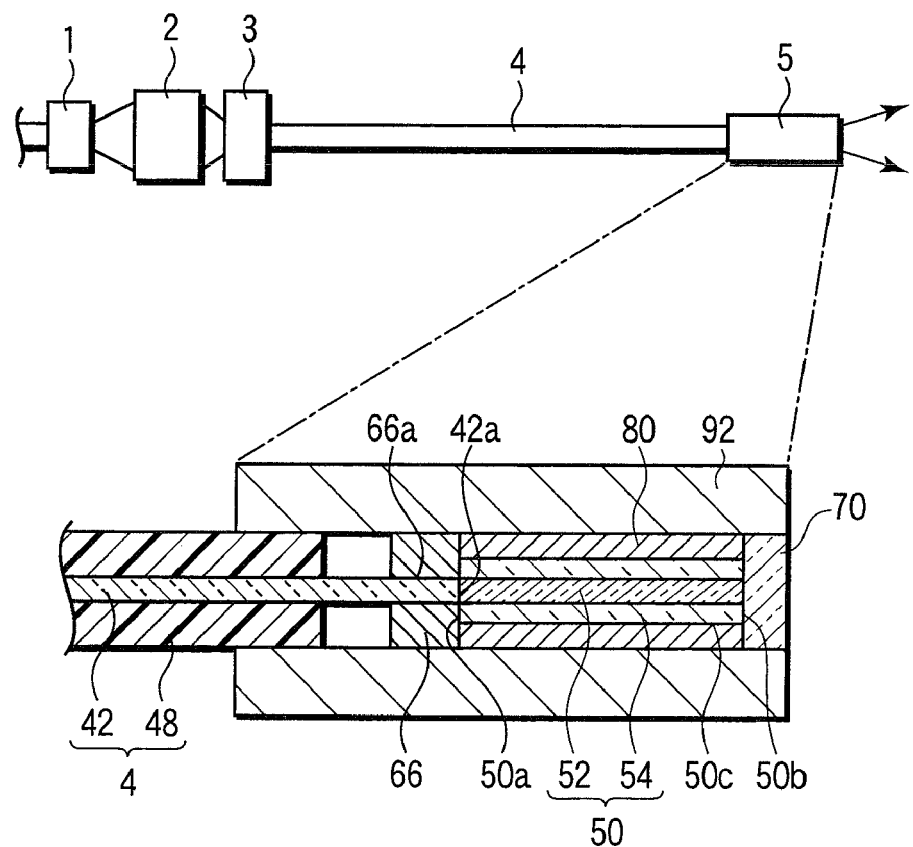
FIG. 4 shows a light source device according to a fourth embodiment of the present invention.

A light source device according to a fourth embodiment of the present invention is shown FIG. 4. In FIG. 4, components provided with the same reference numbers as the components shown in FIG. 3 are similar components and are not described in detail.

The light source device in this embodiment is much the same in organization as the light source device in third embodiment. Parts different from the parts in the third embodiment are chiefly described below.

<Organization>

In the light source device of this embodiment, an incident side optical member 60 is formed by a reflector 66 having a through-hole 66a in the center. In the incident side optical member 60 having this structure, the reflector 66 forms a reflection portion 60b, and the through-hole 66a forms a transmission portion 60a. The reflector 66 has a high reflectance for excitation light and fluorescence. The reflector 66 may be made of, for example, a metal block. The diameter of the through-hole 66a is substantially equal to the diameter of an optical fiber 42, and is approximately 100 to 300 μm. The optical fiber 42 is inserted in the through-hole 66a of the reflector 66, and its emitting end face 42a on the emitting end side is in contact with a high refractive index region 52 of a fluorescent member 50. The optical fiber 42 is aligned with the high refractive index region 52.

<Operation>

In the light source device of this embodiment, the excitation light, which has emitted from the emitting side end face 42a of the optical fiber 42, directly enters the high refractive index region 52 of the fluorescent member 50. The behavior of the excitation light after entering the fluorescent member 50 is similar to the behavior in the third embodiment.

<Advantage>

In the light source device of this embodiment, the end face 42a of the optical fiber 42 on the emitting end side, is in contact with the high refractive index region 52 of the fluorescent member 50, so that the excitation light efficiently enters the high refractive index region 52. Moreover, as in the third embodiment, the excitation light is repeatedly reflected and continues traveling in the fluorescent member 50, and the excitation light has a strong tendency to be confined in the high refractive index region 52 in which the fluorescent substance is doped. Thus, the efficiency of the use of the excitation light for the generation of fluorescence improves. Further, the fluorescence is repeatedly reflected and travels in the fluorescent member 50 before entering the emitting side optical member 70, so that the fluorescence is efficiently guided to the emitting side optical member 70, and the efficiency of the use of the fluorescence for illumination improves.

Fifth Embodiment

Figure 5:
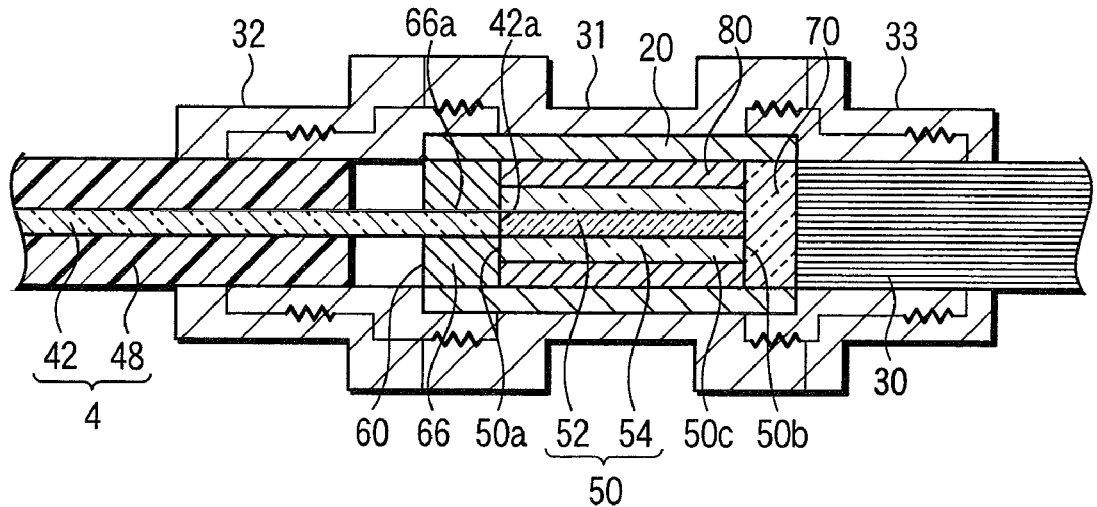
FIG. 5 shows a wavelength converting section of a light source device according to a fifth embodiment of the present invention.

A wavelength converting section of a light source device according to a fifth embodiment of the present invention is shown FIG. 5. In FIG. 5, components provided with the same reference numbers as the components shown in FIG. 4 are similar components and are not described in detail.

<Organization>

In the light source device of this embodiment, a fluorescent member 50, an incident side optical member 60, an emitting side optical member 70, a reflector 80, and an optical fiber code 4 are the same in organization as the equivalents in the fourth embodiment. That is, the incident side optical member 60 is formed by a reflector 66 having a through-hole 66a in the center. An optical fiber 42 is inserted in the through-hole 66a of the reflector 66, and is aligned with a high refractive index region 52. An end face 42a of the optical fiber 42 on the emitting end side is in contact with a high refractive index region 52 of the fluorescent member 50.

The fluorescent member 50, the incident side optical member 60, the emitting side optical member 70, and the reflector 80 are contained in a sleeve 20, and thus contained in a linkage adapter 31. The linkage adapter 31 is shaped in such a way that the central portion of an FC adapter which links existing two FC connectors is elongated 5 to 10 mm to provide a hollow portion. In this hollow portion, the fluorescent member 50, the incident side optical member 60, the emitting side optical member 70, and the reflector 80 are arranged together with the sleeve 20. A connector 32 to which the optical fiber code 4 is fixed is linked to the incident end side of the linkage adapter 31. A connector 33 to which a light guide 30 is fixed is linked to the emitting end side of the linkage adapter 31.

<Operation>

In this embodiment, the linkage adapter 31, and the fluorescent member 50, the incident side optical member 60, the emitting side optical member 70, and the reflector 80, which are contained in the linkage adapter 31, constitute the wavelength converting section. This wavelength converting section is optically coupled to the optical fiber code 4 by linking the connector 32 to the wavelength converting section, and is optically coupled to the light guide 30 by linking the connector 33 to the wavelength converting section. In order to replace the fluorescent member 50, the connectors 32 and 33 are removed from the linkage adapter 31 and linked to another linkage adapter.

The behaviors of excitation light and fluorescence in the wavelength converting section of this embodiment are similar to the behaviors in the third embodiment.

<Advantage>

The fluorescent member 50 can be easily replaced.

Sixth Embodiment

Figure 6:
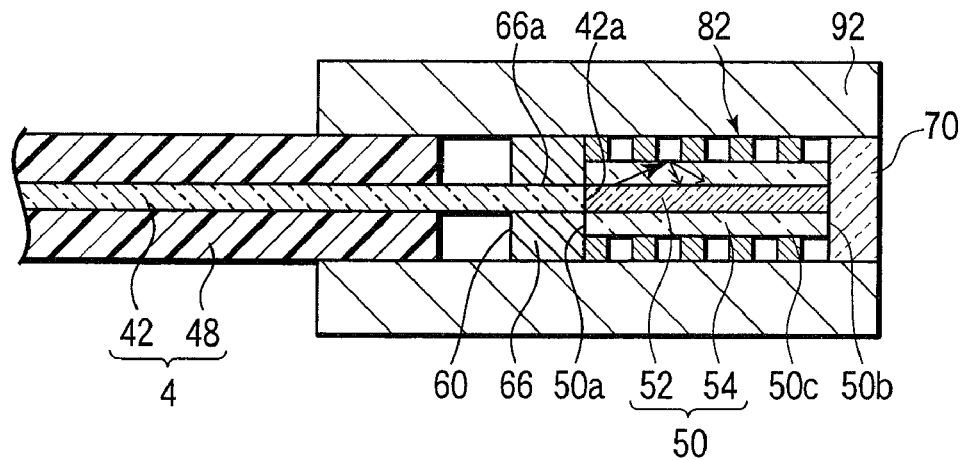
FIG. 6 shows a wavelength converting section of a light source device according to a sixth embodiment of the present invention.

A wavelength converting section of a light source device according to a sixth embodiment of the present invention is shown FIG. 6. In FIG. 6, components provided with the same reference numbers as the components shown in FIG. 4 are similar components and are not described in detail.

<Organization>

The wavelength converting section of the light source device in this embodiment is much the same in organization as the wavelength converting section of the light source device in the fourth embodiment, and is only different therefrom in the organization of the reflector.

In the wavelength converting section of the light source device in this embodiment, a fluorescent member 50, an incident side optical member 60, an emitting side optical member 70, and an optical fiber code 4 are the same in organization as the equivalents in the fourth embodiment. That is, the incident side optical member 60 is formed by a reflector 66 having a through-hole 66a in the center. An optical fiber 42 is inserted in the through-hole 66a of the reflector 66, and is aligned with a high refractive index region 52. An end face 42a of the optical fiber 42 on the emitting end side is in contact with a high refractive index region 52 of the fluorescent member 50.

The wavelength converting section according to this embodiment has a different reflector 82 instead of the reflector 80 in the fourth embodiment. The reflector 82 has a high reflectance for excitation light and fluorescence, and reflects the excitation light and fluorescence back into the fluorescent member 50. The reflector 82 is made of, for example, a metal film or a stack film composed of a metal film and a dielectric film. Moreover, the reflector 82 has, on part of its surface, a diffraction pattern for diffracting the excitation light. This diffraction pattern is designed to reflect the excitation light at a suitable angle and scatter the fluorescence. The suitable angle here is an angle at which the reflected excitation light is again confined into the high refractive index region 52. In this case, a component traveling in the opposite direction from the light traveling toward the emitting side optical member 70 is also generated, but this component is reflected by the reflector 66 which is an incident side optical member 60, and is therefore again returned into the fluorescent member 50.

<Operation>

The wavelength of the excitation light incident to the fluorescent member 50 from the optical fiber code 4 is constant. The excitation light which has entered the reflector 82 is reflected at the suitable angle by the diffraction effect of the diffraction pattern provided in the reflector 82, and again confined into the high refractive index region 52. The fluorescence which has entered the reflector 82 is scattered, and part of the scattered fluorescence travels toward the emitting side optical member 70.

<Advantage>

The excitation light of which reflection angle is controlled by the reflector 82 is more efficiently returned to the high refractive index region 52 than in the fourth embodiment. Thus, the efficiency of the use of the excitation light further improves. Moreover, the fluorescence is scattered by the reflector 82, so that the efficiency of the use of the fluorescence further improves.

Seventh Embodiment

A light source device according to a seventh embodiment of the present invention is shown FIG. 7. In FIG. 7, components provided with the same reference numbers as the components shown in FIG. 2 are similar components and are not described in detail.

The light source device in this embodiment is much the same in organization as the light source device in second embodiment. Parts different from the parts in the second embodiment are chiefly described below.

<Organization>

If the excitation light radiated from an excitation light source 1 has a wavelength of 400 nm or less, certain kinds of fluorescent substances can be efficiently excited. However, human visibility to the light of such a wavelength region is low, and this light is less effective as illumination light. On the other hand, this light may affect the human body, and it is therefore not desirable that this light emitted from the emitting end.

Thus, an excitation light shielding filter 72 for absorbing (not transmitting) excitation light is provided at the subsequent stage of an emitting side optical member 70. This excitation light shielding filter 72 has an optical property of transmitting fluorescence and absorbing excitation light.

<Advantage and Effects>

The excitation light shielding filter is provided at the subsequent stage of the emitting side optical member 70, so that the light source device in this embodiment radiates illumination light which is safely used.

Eighth Embodiment

<Organization>

Figure 8:
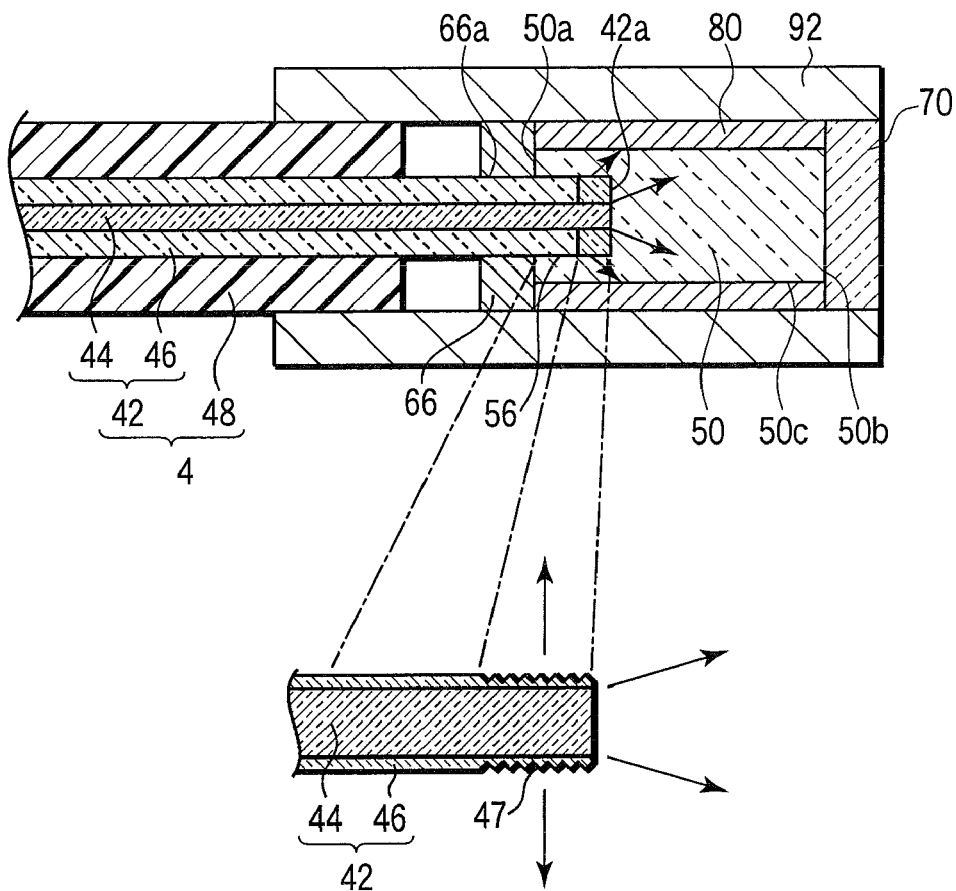
FIG. 8 shows a light source device according to a eighth embodiment of the present invention.

A light source device according to an eighth embodiment of the present invention is shown FIG. 8. In FIG. 8, components provided with the same reference numbers as the components shown in FIG. 2 are similar components and are not described in detail.

In the light source device of this embodiment, an incident side optical member 60 is formed by a reflector 66 having a through-hole 66a in the center. In the incident side optical member 60 having this structure, the reflector 66 forms a reflection portion 60b, and the through-hole 66a forms a transmission portion 60a. The reflector 66 has a high reflectance for excitation light and fluorescence. The reflector 66 may be made of, for example, a metal block. The diameter of the through-hole 66a is substantially equal to the diameter of an optical fiber 42, and is approximately 100 to 300 μm. A fluorescent member 50 has a bore 56 aligned with the through-hole 66a of the reflector 66. The diameter of the bore 56 is also substantially equal to the diameter of the optical fiber 42, and is approximately 100 to 300 μm. The optical fiber 42 is composed of a core 44 and a clad 46 surrounding the core 44. The refractive index of the clad 46 is lower than refractive index of the core 44. The optical fiber 42 is inserted in the through-hole 66a of the reflector 66 and in the bore 56 of the fluorescent member 50. The end of the optical fiber 42, which guided the excitation light to the emitting end side, has a light scattering portion 47 on the side surface of the optical fiber 42. The light scattering portion 47 is composed of, for example, a concavo-convex structure formed on the side surface of the clad 46. Such a concavo-convex structure is formed by, for example, machining or etching. The light scattering portion 47 is located within the bore 56 of the fluorescent member 50.

<Operation>

The beam divergence of excitation light emitted from a normal optical fiber is determined by the difference of relative refractive index between the core 44 and the clad 46. In general, an angle, at which the intensity is half the peak value of the center, is approximately ±30 degrees from the optical center axis. When excitation light having such beam divergence enters the fluorescent member 50, the excitation light travels mainly in an entering direction.

On the other hand, in this embodiment, the end of the optical fiber 42, which guided the excitation light to the emitting end side, has the light scattering portion 47. Therefore, the beam divergence of the excitation light emitted from the optical fiber 42 is significantly great. Moreover, the light scattering portion 47 of the optical fiber 42 is disposed within the bore 56 of the fluorescent member 50. As a result, the excitation light scattered by the light scattering portion 47 is emitted to the fluorescent substance in the fluorescent member 50 over a wide range.

<Advantage>

The excitation light is scattered by the light scattering portion 47 and radiated to the fluorescent member 50 over a wide range. Thus, the efficiency of the use of the excitation light more improves than in the second embodiment.

Ninth Embodiment

Figure 9:
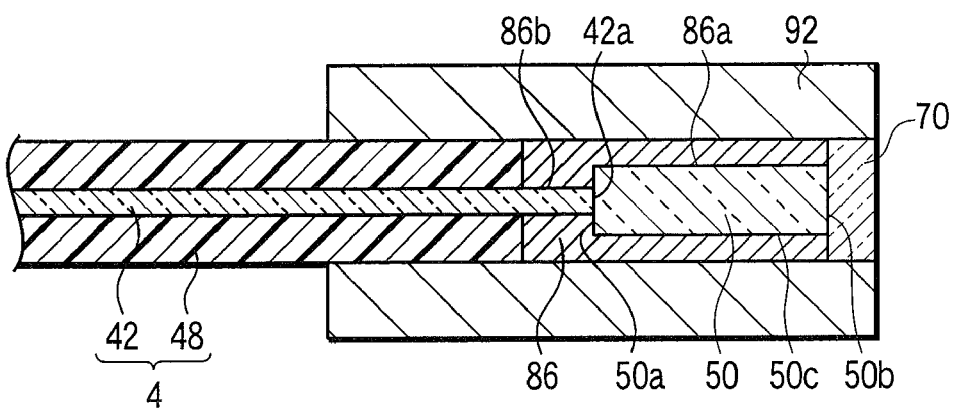
FIG. 9 shows a wavelength converting section of a light source device according to a ninth embodiment of the present invention.
Figure 10:
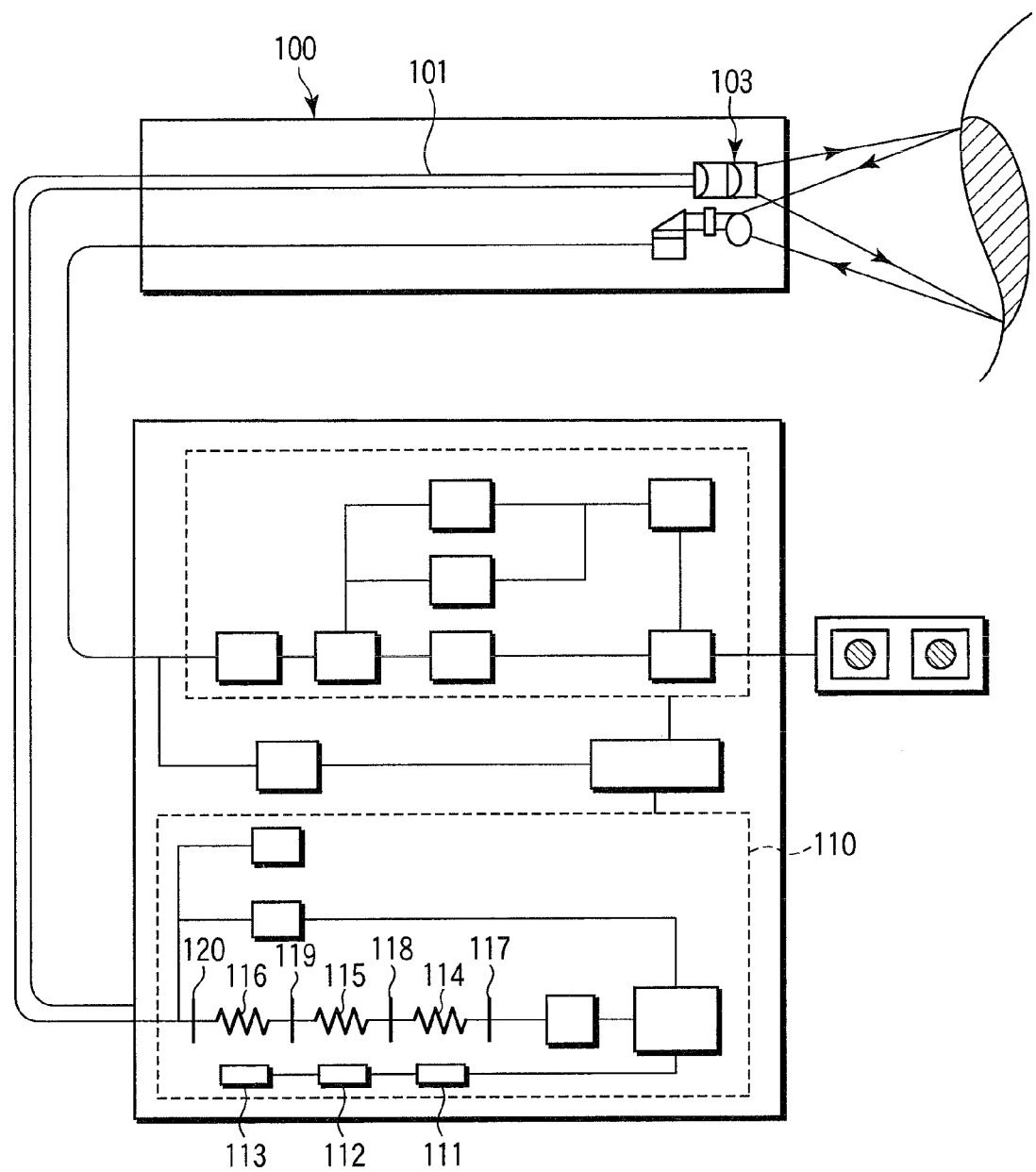
FIG. 10 shows an endoscopic apparatus equipped with a conventional light source device which uses fluorescence.

A wavelength converting section of a light source device according to a ninth embodiment of the present invention is shown FIG. 9. In FIG. 9, components provided with the same reference numbers as the components shown in FIG. 2 are similar components and are not described in detail.

<Organization>

In this embodiment, a fluorescent member 50 is contained in a recess 86a of a hollow member 86 in which a reflector 80 and a reflector 66 are integrated.

A metal film is provided on the inner surface of the recess 86a, and this metal film has a high reflectance for the wavelength ranges of excitation light and fluorescence. The hollow member 86 is contained in a fixing protective portion 92, and the fluorescent member 50 is disposed coaxially with the fixing protective portion 92.

The end of an optical fiber code 4, which guided the excitation light to the emitting end side, is inserted and fixed in the fixing protective portion 92. The optical fiber 42 is inserted in a through-hole 86b of the hollow member 86. An emitting end face 42a of the optical fiber 42, which guided the excitation light to the emitting end side, is in contact with the fluorescent member 50.

An emitting side optical member 70 is disposed on the exit end side of the hollow member 86 containing the fluorescent member 50. The emitting side optical member 70 is inserted and fixed in the fixing protective portion 92.

<Operation>

The excitation light which has emitted from the emitting end face of the optical fiber 42 enters the fluorescent member 50, and part of this excitation light is absorbed by a fluorescent substance, and the fluorescent substance which has absorbed the excitation light generates fluorescence. The fluorescence generated from the fluorescent substance is repeatedly reflected by the hollow member 86 and travels in the fluorescent member 50 before entering the emitting side optical member 70.

Furthermore, another part of the excitation light which has entered the fluorescent member 50 is reflected or scattered by the fluorescent substance or a resin. The reflected or scattered excitation light is repeatedly reflected by the hollow member 86 and the emitting side optical member 70, and travels in the fluorescent member 50.

Since the fluorescent member 50 is surrounded by the hollow member 86, the excitation light and fluorescence which have entered the hollow member 86 are repeatedly reflected in the fluorescent member 50, and emit from the emitting side optical member 70.

<Advantage>

The excitation light and fluorescence which have entered the hollow member 86 are repeatedly reflected in the fluorescent member 50, and then emit from the emitting side optical member 70. Thus, the efficiency of the use of the excitation light and fluorescence further improves.

While the embodiments of the present invention have been described above with reference to the drawings, the present invention is not limited to these embodiments. Various modifications and alterations may be made without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
   an excitation light source which generates excitation light;
   a fluorescent member containing a fluorescent substance which absorbs the excitation light to generate fluorescence;
   an emitting side optical member which is provided on an emitting end face of the fluorescent member and which has an optical property of reflecting the excitation light and transmitting the fluorescence;
   a reflector which is provided on the side surface of the fluorescent member and which has an optical property of reflecting the excitation light and the fluorescence;
   an incident side optical member provided on an incident end face of the fluorescent member, the incident side optical member including a transmission portion which has an optical property of transmitting the excitation light, and a reflection portion which has an optical property of reflecting the excitation light and the fluorescence; and an optical fiber which guides the excitation light generated from the excitation light source to the incident side optical member, the incident side optical member including a through-hole, the through-hole forming the transmission portion, the optical fiber being inserted in the through-hole of the incident side optical member.

2. The light source device according to claim 1, wherein the fluorescent member includes a bore aligned with the through-hole of the incident side optical member, the optical fiber being inserted in the through-hole and the bore, an end of the optical fiber on an emitting end side including a light scattering portion on the side surface of the optical fiber, the light scattering portion being located in the bore of the fluorescent member.

* * * * *